United States Patent [19]

Ludvik

[11] Patent Number: 4,675,447

[45] Date of Patent: Jun. 23, 1987

[54] METHOD FOR PREPARATION OF ALKYLSULFONYL ALKYLCHLOROBENZENES

[75] Inventor: Charles N. Ludvik, Oakland, Calif.

[73] Assignee: Stauffer Chemical Company, Westport, Conn.

[21] Appl. No.: 842,693

[22] Filed: Mar. 21, 1986

[51] Int. Cl.⁴ .................... C07C 147/06; C07B 39/00
[52] U.S. Cl. .................................... 568/28; 260/694
[58] Field of Search ..................... 568/28, 35; 260/694

[56] References Cited

U.S. PATENT DOCUMENTS

| | | | |
|---|---|---|---|
| 2,302,228 | 11/1942 | Kharasch et al. | 260/694 |
| 2,777,002 | 1/1957 | Sullivan | 568/64 |
| 3,879,472 | 4/1975 | Martin | 568/28 |
| 4,345,097 | 8/1982 | Howard et al. | 562/472 |
| 4,386,221 | 5/1983 | Hyatt et al. | 568/35 |

FOREIGN PATENT DOCUMENTS 193200 2/1923 United Kingdom .

OTHER PUBLICATIONS

O. Silberad, J. Chem. Soc., London, 119, 2029–2036 (1921).

H. Kugita et al, Chem. Abstracts, vol. 62 (1965), p. 6422e.

Primary Examiner—Mary E. Ceperley
Attorney, Agent, or Firm—Joel G. Ackerman

[57] ABSTRACT

An improved process for the production of compounds having the formula

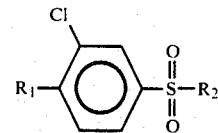

in which $R_1$ and $R_2$ are lower alkyl by reacting a compound having the formula

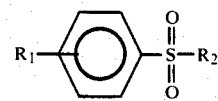

with sulfuryl chloride in the presence of a catalytic amount of a metal halide, the improvement in the process being reducing undesired impurities.

8 Claims, No Drawings

METHOD FOR PREPARATION OF ALKYLSULFONYL ALKYLCHLOROBENZENES

BACKGROUND OF THE INVENTION

Compounds of the type

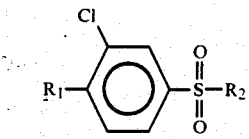

wherein $R_1$ and $R_2$ are lower alkyl are useful intermediates in the synthesis of pesticides such as herbicides containing an alkylsulfonylphenyl group. Prior art discloses production of one of these compounds, namely 2-chloro-4-methylsulfonyltoluene, by chlorination of 4-methylsulfonyltoluene with chlorine gas in the presence of antimony trichloride catalyst. We found that this process was not entirely satisfactory due to the difficulties in handling chlorine gas and the formation of undesirable impurities, which we determined resulted partially from dichlorination of the ring.

Standard methods of eliminating the undesirable impurities were not satisfactory. We have now discovered that the undesired dichlorinated and other impurities which are formed when using chlorine gas as a chlorinating agent can be greatly reduced by instead employing sulfuryl chloride as a chlorinating agent.

SUMMARY OF THE INVENTION

This invention comprises a process for the production of compounds having the formula

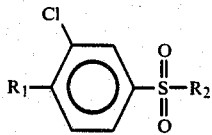

in which $R_1$ and $R_2$ are lower alkyl, by reaction of a compound having the formula

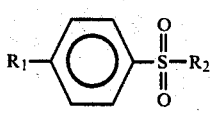

with sulfuryl chloride in the presence of a catalyst.

DESCRIPTION OF THE INVENTION

The products of this process have the general formula

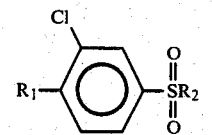

wherein $R_1$ and $R_2$ are lower alkyl, preferably $C_1$–$C_4$ alkyl groups. $R_1$ and $R_2$ may be the same or different and are, for instance, methyl, ethyl, n-propyl, isopropyl, n-butyl, secondary butyl, isobutyl or tertiary butyl. A preferred product is that in which $R_1$ is methyl.

It has been found that dichlorinated and other impurities can be reduced from amounts which range from about 10–15% when using chlorine gas as the chlorinating agent to as little as about 4% using sulfuryl chloride in the presence of a catalyst. This reduction in dichlorinated and other impurities eliminates the need for purification of the product when used as an intermediate.

The catalyst which may be used in this process are preferably metal halides, and most preferably Lewis acids such as aluminum chloride, ferric chloride, zinc chloride and antimony trichloride.

This reaction proceeds at a temperature ranging from about 50° C. to about 120° C., preferably from about 50° to about 95° C., most preferably from about 80° to about 95° C., and at a pressure from about one to about three atmospheres.

The invention is further illustrated by the following examples.

EXAMPLE I

Sixty-five grams (65 g, 0.38 mole) of molten p-(methylsulfonyl) toluene and 6.1 g (0.027 mole) antimony trichloride were placed in a reactor equipped with a condenser, scrubber, mechanical stirrer, heating mantle, dropping funnel and nitrogen purge. Sulfuryl chloride (155 g, 1.15 mole) was added dropwise throughout the reaction while heating the mixture and allowing the refluxing sulfuryl chloride to maintain the temperature between 90° C. and 92° C. The heat was removed on completion of the reaction and a vigorous nitrogen purge was then begun and allowed to continue overnight to remove excess sulfuryl chloride.

The product was isolated by extraction with 180 milliliters (ml) of dichloromethane, washed with 100 ml water, 100 ml of 5% sodium hydroxide and another 100 ml of water. The organic phase was then evaporated under reduced pressure to yield 63 g of solids with a melting point range of 85°–89° C. Structure was confirmed by gas chromatography which determined the purity to be about 96%.

EXAMPLE II

Sixty-five grams (65 g, 0.38 mole) of molten p-(methylsulfonyl)-toluene and 4.3 g (0.027 mole) ferric chloride were placed in a reactor equipped with a condenser, scrubber, mechanical stirrer, heating mantle, dropping funnel and nitrogen purge. Sulfuryl chloride (94 ml, 1.17 mole) was added throughout the reaction while heating the mixture and allowing the refluxing sulfuryl chloride to maintain the temperature between 90° C. and 92° C. The heat was removed on completion of the reaction.

The product was isolated by extraction with 200 ml of dichloromethane, washed with 200 ml of water, 102 ml of 5% sodium hydroxide and another 100 ml of water. The organic phase was then evaporated under reduced pressure to yield 62 g of solids with a melting point range of 85°–89° C. Structure was confirmed by Gas chromatography, infrared, nuclear magnetic resonance and mass spectroscopy. Gas chromatograph determined the purity to be about 95.8%.

What is claimed is:

1. A process comprising reacting a compound having the formula

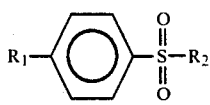

wherein $R_1$ and $R_2$ are lower alkyl with sulfuryl chloride in the presence of a Lewis acid metal halide catalyst to produce a compound having the formula

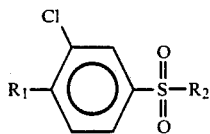

wherein $R_1$ and $R_2$ are as defined.

2. A process according to claim 1 wherein the catalyst is aluminum trichloride, antimony trichloride, ferric chloride or zinc chloride.

3. A process according to claim 1 wherein $R_1$ and $R_2$ are lower alkyl of 1 to 4 carbon atoms, straight chain or branched, and are the same or different.

4. A process according to claim 1 wherein $R_1$ and $R_2$ are methyl.

5. A process according to claim 1 wherein the temperature is from about 50° C. to about 120° C.

6. A process according to claim 1 wherein the temperature is from about 50° C. to about 95° C.

7. A process according to claim 1 wherein the temperature is from about 80° C. to about 95° C.

8. A process according to claim 1 conducted in the absence of a solvent.

* * * * *